(12) United States Patent
Chappo et al.

(10) Patent No.: US 11,076,809 B2
(45) Date of Patent: Aug. 3, 2021

(54) STATIC CHARGE FILTER FOR CARDIAC ELECTRICAL SIGNALS CORRUPTED WITH STATIC CHARGE AND ROUTED TO AN ELECTROCARDIOGRAPH (EKG) MONITOR

(71) Applicant: KONINKLIJKE PHILIPS N.V., Eindhoven (NL)

(72) Inventors: Marc Anthony Chappo, Elyria, OH (US); David Dennis Salk, Parma, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 225 days.

(21) Appl. No.: 15/778,872

(22) PCT Filed: Dec. 2, 2016

(86) PCT No.: PCT/EP2016/079682
§ 371 (c)(1),
(2) Date: May 24, 2018

(87) PCT Pub. No.: WO2017/093546
PCT Pub. Date: Jun. 8, 2017

(65) Prior Publication Data
US 2018/0353135 A1   Dec. 13, 2018

Related U.S. Application Data

(60) Provisional application No. 62/262,541, filed on Dec. 3, 2015.

(51) Int. Cl.
*A61B 5/00* (2006.01)
*A61B 5/0428* (2006.01)
(Continued)

(52) U.S. Cl.
CPC .............. *A61B 5/7207* (2013.01); *A61B 5/30* (2021.01); *A61B 5/339* (2021.01); *A61B 5/352* (2021.01);
(Continued)

(58) Field of Classification Search
CPC .... A61B 5/7203; A61B 5/7225; A61B 5/0428
See application file for complete search history.

(56) References Cited

U.S. PATENT DOCUMENTS 4,149,527 A   4/1979 Naylor
4,448,202 A   5/1984 Wajszczuk
(Continued)

FOREIGN PATENT DOCUMENTS

CN   1596825    3/2005
GB   2181554    4/1987
WO   2000065994  11/2000

*Primary Examiner* — Gary Jackson
*Assistant Examiner* — Zahed Kabir
(74) *Attorney, Agent, or Firm* — Larry Liberchuk

(57) ABSTRACT

A static charge filter (522) removes static charge in a cardiac electrical signal. The static charge filter includes a first amplifier (608) configured to amplify an input signal, which includes the cardiac electrical signal and static charge from an electrode, which is in a path of an X-ray beam. The static charge filter further includes a limiter (614) configured to limit a maximum voltage of the signal based on a predetermined clamping threshold, producing a voltage clamped signal. The static charge filter further includes a filter (616) configured to filter high frequency components of the voltage clamped signal, producing a filtered signal. The static charge filter further includes a second amplifier (620) configured to scale an amplitude of the filtered signal so that cardiac electrical signal in an output signal has a same voltage level as a voltage level of the cardiac electrical signal in the input signal.

17 Claims, 5 Drawing Sheets

(51) Int. Cl.
  *A61B 6/03* (2006.01)
  *A61B 5/0456* (2006.01)
  *A61B 5/044* (2006.01)
  *A61B 6/00* (2006.01)
  *A61B 5/30* (2021.01)
  *A61B 5/339* (2021.01)
  *A61B 5/352* (2021.01)

(52) U.S. Cl.
  CPC .......... *A61B 5/7203* (2013.01); *A61B 5/7225* (2013.01); *A61B 5/7289* (2013.01); *A61B 5/7292* (2013.01); *A61B 6/032* (2013.01); *A61B 6/5288* (2013.01); *A61B 6/541* (2013.01)

(56) References Cited

U.S. PATENT DOCUMENTS

| | | | |
|---|---|---|---|
| 4,800,894 A | 1/1989 | Milani | |
| 5,417,221 A | 5/1995 | Sickler | |
| 7,039,455 B1 | 5/2006 | Brosovich | |
| 2004/0042581 A1 | 3/2004 | Okerlund | |
| 2010/0253319 A1* | 10/2010 | Cehelnik | G06F 3/0443 324/72 |
| 2012/0330557 A1* | 12/2012 | Zhang | A61B 6/503 702/19 |
| 2014/0200469 A1* | 7/2014 | Bocko | A61B 5/0245 600/509 |
| 2014/0316231 A1 | 10/2014 | Luhta | |

* cited by examiner

STATIC CHARGE FILTER FOR CARDIAC ELECTRICAL SIGNALS CORRUPTED WITH STATIC CHARGE AND ROUTED TO AN ELECTROCARDIOGRAPH (EKG) MONITOR

CROSS REFERENCE TO RELATED APPLICATIONS

This application is the U.S. National Phase application under 35 U.S.C. § 371 of International Application No. PCT/EP2016/079682, filed Dec. 2, 2016, published as WO 2017/093546 on Jun. 8, 2017, which claims the benefit of U.S. Provisional Patent Application No. 62/262,541 filed Dec. 3, 2015. These applications are hereby incorporated by reference herein.

FIELD OF THE INVENTION

The following generally relates to a static charge filter for cardiac electrical signals corrupted with static charge and routed to an electrocardiograph (EKG) monitor, and is described with particular application to computed tomography (CT), where EKG electrodes and/or leads in a path of an X-ray radiation beam accumulate charge, which is discharged by the X-ray radiation through the leads, corrupting the cardiac electrical signals routed through the leads to the EKG monitor.

BACKGROUND OF THE INVENTION

Cardiac gated Computed tomography (CT) generally requires a CT scanner, an electrocardiograph (EKG) monitor, patient electrodes, and leads that mechanically connect to and that electrically connect the electrodes and the EKG monitor. The EKG electrodes sense electrical changes on the skin that arise from the heart muscle depolarizing during each heartbeat. The electrical charge is transferred via the EKG electrodes to the leads, which routes the electrical charge to the EKG monitor, which processes the charge and produces an EKG waveform indicative of electrical activity of each heart beat or cycle, which reflects a state of the heart throughout the heart cycle. FIG. 1 shows an example of a "normal" waveform 100 for three cardiac cycles 102, 104 and 106, where a y-axis represents amplitude (e.g., in millivolts) and an x-axis represents time.

In FIG. 1, each of the cardiac cycles 102-106 has a systolic period 108 in which the atria (P wave 110) and subsequently the ventricles (QRS complex 112) contract and the ventricles then re-polarize (the T wave 114), and a diastolic period 116 in which the heart relaxes and refills with circulating blood. For prospectively gated cardiac CT, an R peak 118 of the QRS complex 112 is identified in the waveform 100, e.g., based on its amplitude, and used to trigger a scan for a predetermined acquisition window within a quiet phase 120 of the heart in which motion of the heart is relative low compared to the motion during other phases of heart. For retrospectively gated cardiac CT, the heart is scanned and the projection data is synchronized with the waveform 100 so that after the scan the R peak 118 can be identified and used to retrieve projection data for the acquisition window. In both instances, multiple images for the window but different cycles can be reconstructed.

The number and placement of the electrodes on the patient depends on whether a 3, 4, 5 or 12-lead configuration is used. FIG. 2 show an example of EKG electrode placement on a patient 200 relative to the heart 202 for a 4-lead configuration. The illustrated configuration includes a right arm electrode 204, a left arm electrode 206, a right leg electrode 208 and a left leg electrode 210. With this configuration, the entire heart 202 can be scanned without any of the electrodes 204-210 in a path 212 of the X-ray beam. FIG. 3 shows an example where all of the electrodes but one (the electrode 208) are in the path 212 of the X-ray beam. Unfortunately, electrodes and/or leads in the X-ray beam accumulate static charge, and the X-ray radiation discharges the charge (via electrostatic discharge, or ESD), which results in a voltage spike or pulse that ultimately corrupts the EKG waveform. FIG. 4 shows an example of a corrupted waveform.

The waveform 400 of FIG. 4 is substantially the same as the waveform of FIG. 1, except the waveform 400 include a voltage spike 402, which has an amplitude at least a large as that of the R peak 118. In this example, the amplitude of the spike 402 is approximately two and a half times the amplitude of the R peak 118 and in the opposite direction (i.e., negative). However, such spikes may be larger or smaller, and/or positive. Unfortunately, the spike 402 may be identified as an R peak. With prospectively gated cardiac CT, a false R peak may trigger a scan that is at least partially outside of the acquisition window within the quiet phase. With retrospectively gated cardiac CT, the false R peak may lead to reconstructing projection data acquired at least partially outside of the acquisition window within the quiet phase. In either instance, this may result in degradation of image quality (increased motion), possibly to the extent that the final image is not diagnostic quality, even though the patient has been irradiated.

One approach to mitigating such static charge is to keep the electrodes and leads out of the beam path. Unfortunately, this is not always feasible, e.g., where the electrodes are already on a patient in an emergency situation. Another approach includes applying a contact gel to the electrodes before scanning to provide a discharge path. Likewise, this approach is not always feasible. Furthermore, it requires access to contact gel and adds additionally scan preparation steps and cost. Another approach is to use carbon impregnated electrodes and leads which bleed off charge before it is large enough to corrupt the cardiac electrical signals. Such electrodes are described in US 20140316231 A1 to Luhta et al. Unfortunately, such electrodes are customized and may add cost, which may deter a facility from procuring them, especially with the small percentage of cases that require them.

SUMMARY OF THE INVENTION

Aspects described herein address the above-referenced problems and/or others.

In one aspect, a static charge filter removes static charge in a cardiac electrical signal. The static charge filter includes a first amplifier configured to amplify an input signal, which includes the cardiac electrical signal and static charge from an electrode, which is in a path of an X-ray beam. The static charge filter further includes a limiter configured to limit a maximum voltage of the signal based on a predetermined clamping threshold, producing a voltage clamped signal. The static charge filter further includes a filter configured to filter high frequency components of the voltage clamped signal, producing a filtered signal. The static charge filter further includes a second amplifier configured to scale an amplitude of the filtered signal so that cardiac electrical signal in an output signal has a same voltage level as a voltage level of the cardiac electrical signal in the input signal.

In another aspect, a system includes a gantry with an examination region, an X-ray radiation source configured to produce and transmit X-ray radiation that traverses the examination region, an X-ray sensitive detector array configured to detect X-ray radiation traversing the examination region and generate projection data, and a reconstructor configured to reconstruct at least a sub-portion of the projection data and generate an image indicative thereof. The system further includes a static charge filter configured to receive cardiac electrical signals sensed by electrodes in the examination region, wherein at least one of the electrodes is in a path of the X-ray radiation traversing the examination region and remove static charge from the cardiac electrical signal.

In another aspect, a method includes receiving a cardiac electrical signal from an electrode in a path of an X-ray beam during an imaging examination, wherein the cardiac electrical signal includes static charge. The method further includes removing a static charge voltage spike from the received cardiac electrical signal, producing a static charge filtered cardiac electrical signal. The method further includes transmitting the static charge filtered cardiac electrical signal to an EKG monitor, which processes the static charge filtered cardiac electrical signal and produces an EKG waveform representing an electrical activity of a heart of the subject.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF EMBODIMENTS

Figure 5:
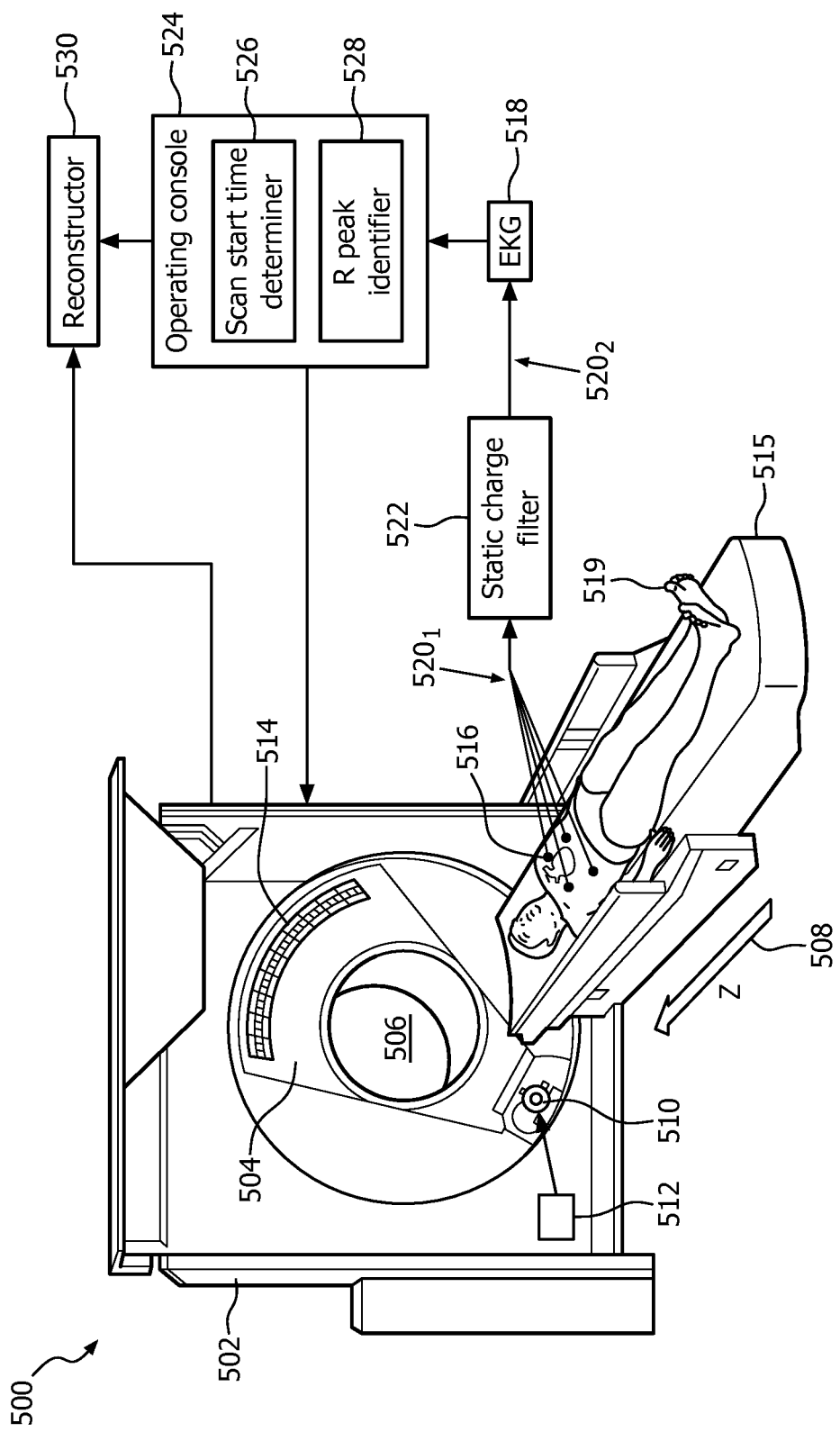
FIG. 5 schematically illustrates an example system including an imaging scanner, and EKG device, and a static charge filter.

FIG. 5 illustrates an imaging system 500 such as a computed tomography (CT) scanner. The illustrate system 500 includes a generally stationary gantry 502 and a rotating gantry 504. The rotating gantry 504 is rotatably supported by the stationary gantry 502 via a bearing or the like and rotates around an examination region 506 about a longitudinal or z-axis 508 and emits radiation.

A radiation source 510, such as an x-ray tube, is supported by the rotating gantry portion 504 and rotates therewith. The radiation source 510, as it rotates around the examination region 506, emits radiation that traverse the examination region 506. The radiation source 510 can also emit radiation while the rotating gantry 504 is at a static position, for example, for a pilot, scout, axial, and/or other scan.

A radiation source controller 512 selectively turns radiation on and off. For example, the radiation source controller 512 can "gate" the radiation source 510, based on a gating signal, to selectively turn x-rays on to acquire data only in an acquisition window. For example, the gating signal can be generated in response to detecting an R peak in an EKG signal and cause the imaging system 500 scan the heart during a predetermined acquisition window during a quiet phase of the heart for a gate cardiac CT scan.

An X-ray radiation sensitive detector array 514 subtends an angular arc opposite the examination region 506 relative to the radiation source 510. The illustrated X-ray radiation sensitive detector array 514 includes a one or two-dimensional array of photosensitive pixels. The X-ray radiation sensitive detector array 514 detects The X-ray radiation traversing the examination region 506 and generates projection data, or a signal, indicative thereof.

A subject support 515, such as a couch, supports a subject, such as a human or animal, or an object within the examination region 506. The subject support 515 is movable horizontally and/or vertically, which enables an operator or the system to load a subject, suitably position the subject within the examination region 506 before, during and/or after scanning, and unload the subject.

EKG electrodes 516 are attached to a patient 519 and sense electrical signals of the heart (cardiac electrical signals). A first set of leads $520_1$ routes the cardiac electrical signals from the EKG electrodes 516. Where static charge is present and discharged from the EKG electrodes 516 and/or the first set of leads $520_1$ by the X-ray beam and/or otherwise, the static charge corrupts the cardiac electrical signals (e.g., with one or more spikes 402 shown in FIG. 4), and the first set of leads $520_1$ routes the corrupted cardiac electrical signal, which includes the cardiac electrical signals and static charge spikes.

Figure 1:
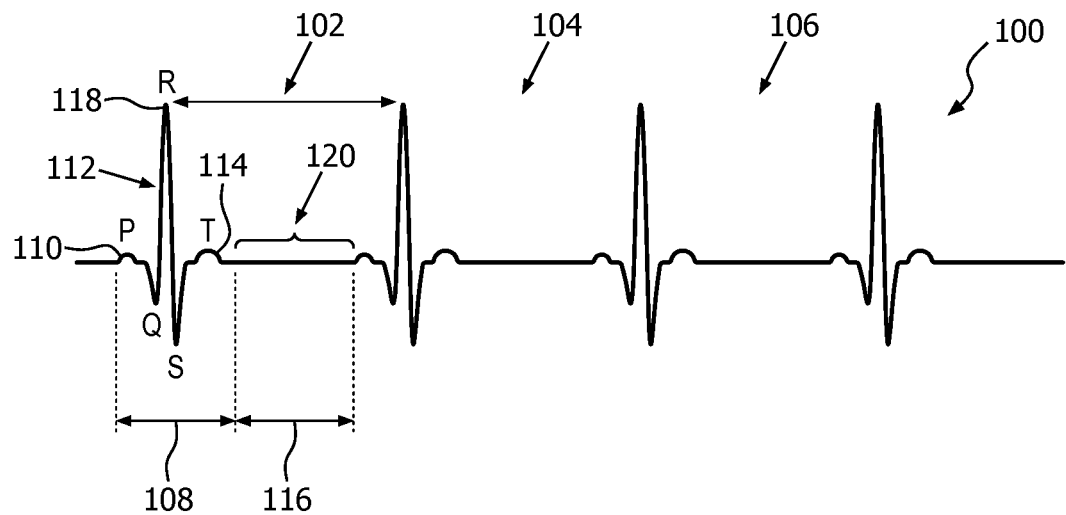
FIG. 1 schematically illustrates an example "normal" a EKG waveform.

A static charge filter 522 is connected to the other end of the first set of leads $520_1$, receives the corrupted cardiac electrical signals, filters the corrupted cardiac electrical signal to remove static charge, and outputs filtered cardiac electrical signals, which are essentially free of static charge that may result in a false R peak. A second set of leads $520_2$ routes the filtered cardiac electrical signals from the static charge filter 522. An EKG monitor 518 is connected to the other end of the second set of leads $520_2$, and processes the filtered cardiac electrical signals and generates an EKG waveform similar to the waveform 100 shown and described in connection with FIG. 1.

As described in greater detail below, in one instance the static charge filter 522 includes active circuitry that amplifies an input corrupted cardiac electrical signal, clamps a maximum allowable voltage amplitude of the amplified signal, low pass filters high frequency components resulting from the clamping, and scales the voltage amplitude of the filtered signal to a level of the input cardiac electrical signals, to remove static charge. Thus, with prospectively and/or retrospectively gated cardiac CT, a voltage spike due to static charge will not be identified in the signal output by the static charge filter 522 as an R peak and used as a trigger. As such, the image quality of the reconstructed images will not be degraded due to static charge when an electrode(s) of the electrodes 516 and/or a lead(s) of the first set of leads 520₁ is in the path of the X-ray beam during scanning.

A computing system serves as an operator console 524 and allows a user to select an imaging protocol such as a prospectively and/or retrospectively gated cardiac CT protocol. The illustrated operator console 524 includes an R peak identifier 528 and a scan start time determiner 526. The R peak identifier 528 identifies R peaks in the EKG waveform and generates a trigger signal indicative thereof for both prospectively and retrospectively gated scans. For prospectively gated scans, a scan start time determiner 526 determines a start time for an acquisition window based on the trigger signal and/or other information such as a time delay from the R peak. In a variation, the R peak identifier 528 is located in the EKG 518 and/or other device. Where the system is configured only for retrospectively gated cardiac CT scans, the scan start time determiner 526 can be omitted.

A reconstructor 530 reconstructs the projection data and generates volumetric image data indicative thereof. For prospectively gated cardiac CT, this includes reconstructing the projection data for the scan of the acquisition window within the quiet phase triggered by the R peak of the EKG waveform from the filtered cardiac electrical signals. For retrospectively gated cardiac CT, this includes identifying projection data corresponding to the acquisition window within the quiet phase based on the filtered cardiac electrical signals, which is synchronized with the projection data from the scan. The resulting volumetric image data can be visually presented via a display monitor, stored in a data repository (e.g., a picture and archiving communication system, or PACS), etc.

Figure 6:
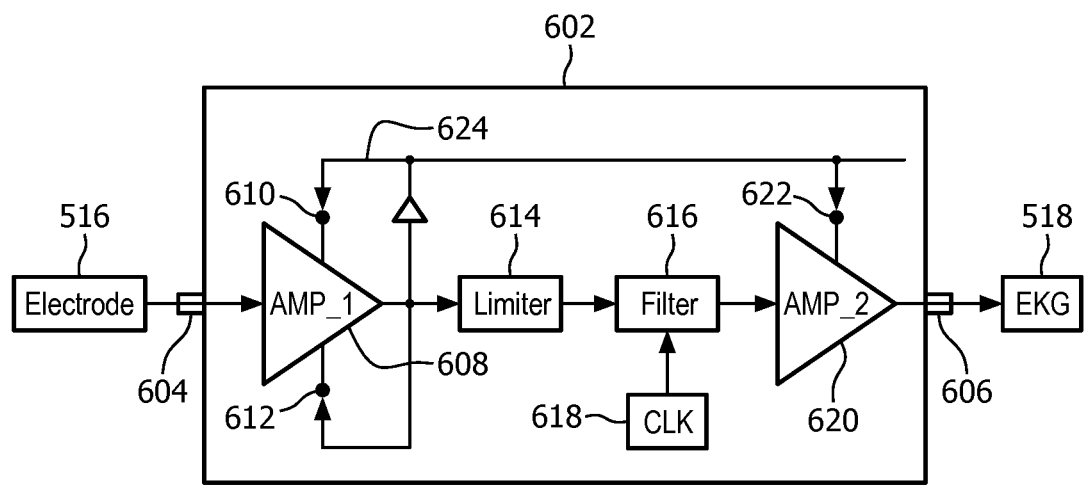
FIG. 6 schematically illustrates an example of the static charge filter.

FIG. 6 schematically illustrates an example channel 602 of the static charge filter 522.

In one instance, the static charge filter 522 includes a channel for each EKG electrode. For example, the static charge filter 522 for a 4 lead EKG will include at least 4 channels, etc. In one configuration, each channel filters a corresponding one of the input cardiac electrical signals. This configuration is well-suited for EKGs which can vary which set of the electrical signals is used to identify the R peak. In another configuration, where a signal from a predetermined particular electrode is used to identify the R peak, only the channel corresponding to the particular electrode includes the filter, and the other channels are pass-throughs.

Figure 7:
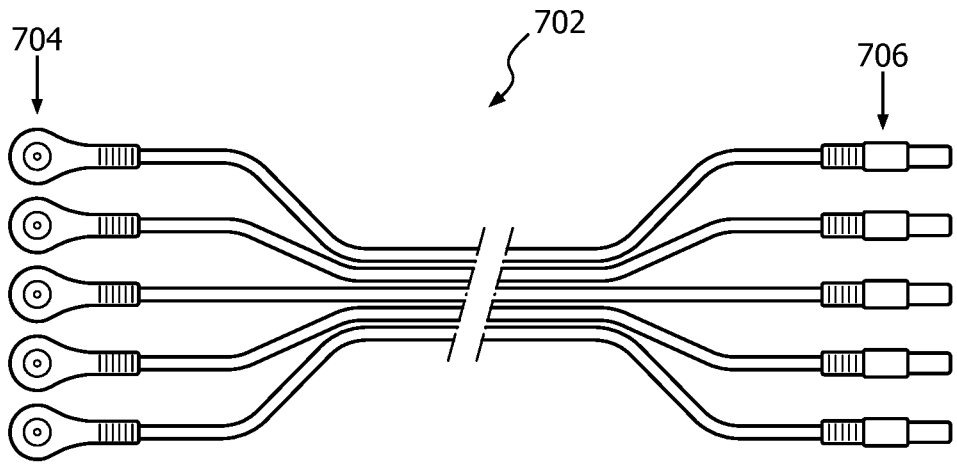
FIG. 7 shows an example set of EKG leads.

The illustrated channel 602 includes an input connector 604 and an output connector 606. In one instance, the input connector 604 is configured the same as an input connector of the EKG monitor 518, and the output connector 606 is configured the same as connector of the electrode 516. In this manner, a same cable utilized without the static charge filter 522 to electrically connect the EKG electrodes 516 to the EKG 518 can be used to connect the EKG electrodes 516 to the static charge filter 522 and the static charge filter 522 to the EKG 518. FIG. 7 shows an example cable 702 with electrode connectors 704 and EKG connectors 706 for a 5-lead EKG. Other types of connectors (e.g., BNC, etc.) are also contemplated herein.

The illustrated channel 602 further includes a first amplifier 608 that amplifies the input signal. The first amplifier 608 includes a first gain input 610 and an offset input 612. A limiter 614 is configured to clip or limit the amplified voltage of the amplified signal. A clocked filter 616 and a clock 618 filters the clipped signal. A second amplifier 620 with a second gain input 622 scales the filtered signal. A first gain of the first amplifier 608 is set to ensure the cardiac electrical signal is amplified near a clipping threshold of the limiter 614 so that spikes 402 (FIG. 4) due to X-ray static discharge events are clamped by the limiter 614, which generates out of band harmonics. Automatic gain control is achieved through a feedback loop 624. The offset input is configured to monitor the root-mean-square (RMS) and/or other statistical measure and keep the offset voltage close to zero.

Figure 8:
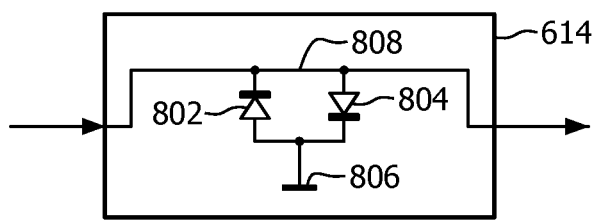
FIG. 8 schematically illustrates an example of a voltage limiter of the static charge filter.

FIG. 8 schematically illustrates an example of a suitable limiter 614. In this example, the limiter 614 includes two diodes 802 and 804 in parallel (in reverse polarity) with one of the sides connected to electrical ground 806 and the other of the sides connected the an electrically conductive pathway 808 through the limiter 614. With this configuration, as long as the amplitude of the input signal does not exceed the reverse bias voltage of the diodes, the diodes remain off and the signal passes through. However, when the amplitude of the signal exceeds the reverse bias voltage of one of the diodes, that diode turns on and shorts to the electrical ground 806. As such, the limiter 614 clamps the signal such that the output signal never exceeds the reverse bias voltage. Other voltage limiting circuitry is also contemplated herein.

Returning to FIG. 6, a suitable filter 616 is a clock programmable (switched capacitor) low pass filter. In this example, the filter 616 is a high order low pass type filter that rejects higher frequency content, or the out of band harmonics generated after the limiter 614 clamps the signal. The filtered signal is substantially free of the static discharge seen by the electrodes in the X-ray beam. The second amplifier 620 is a low output impedance amplifier configured with a second gain that scales the processed signal to match the levels of the input electrical signal. In one instance, where the first gain of the first amplifier 608 is A, the second gain of the second amplifier 620 is 1/A. In another instance, the second gain of the second amplifier 620 is 1/A+internal losses.

The circuitry implementation of the channel 602 can be realized in a standard CMOS fab processing steps of an ASIC, Commercial-Off-The-Shelf (COTS) components, and/or otherwise. COTS components may include power supply regulators, low-offset operational amplifiers (Op-Amps), clock-programmable filters, limiter circuits including simple versions with diode clamps, and standard discrete capacitors and resistors with printed circuit (PC) card and standard connectors and wiring. Power can be supplied by the EKG 518, the imaging system 500, an internal (rechargeable or non-rechargeable) battery, AC power from a wall receptacle, AC and/or DC power from a power supply, and/or other power source.

The following provides a non-limiting example.

Figure 2:
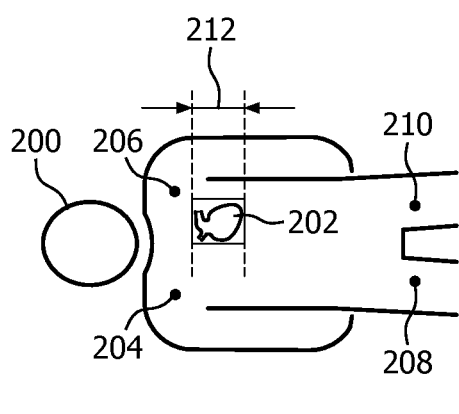
FIG. 2 schematically illustrates example placement of EKG electrodes on a patient outside of the X-ray beam path.
Figure 4:
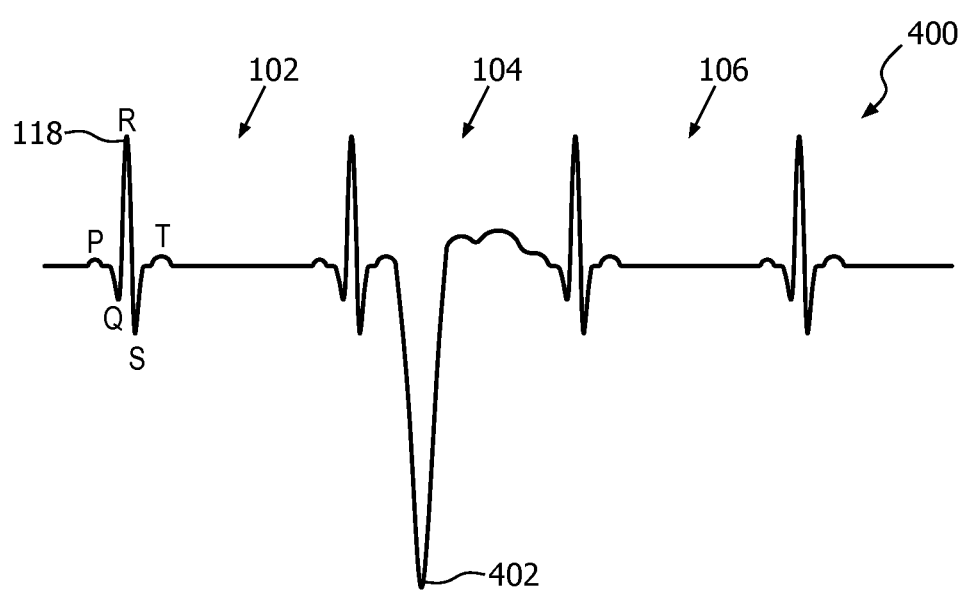
FIG. 4 schematically illustrates an example of a EKG waveform corrupted with static charge from an EKG electrode and/or lead in the X-ray beam path.

For this example, the amplitude of the R peaks 118 (FIG. 1) in the cardiac electrical signals from the electrodes 204-210 (FIG. 2) is in a millivolt (mV) range. The two diodes 802 and 804 (FIG. 8) have a reverse bias voltage of 0.7V (0.3V for germanium diodes). The first gain is A=1000, and the second gain is 1/1000. In this instance, the voltage of the amplified signal will be clamped at ±0.7V, and the spike 402 will be removed regardless of whether it is positive or negative (e.g., as shown in FIG. 4). After low pass filtering the high frequency odd harmonics, the filtered signal is scaled by the second gain, and the output signal will be in the millivolt range like the input signal. Where there is no spike 402 (FIG. 4), the channel 602 essentially behaves as a pass through.

Figure 9:
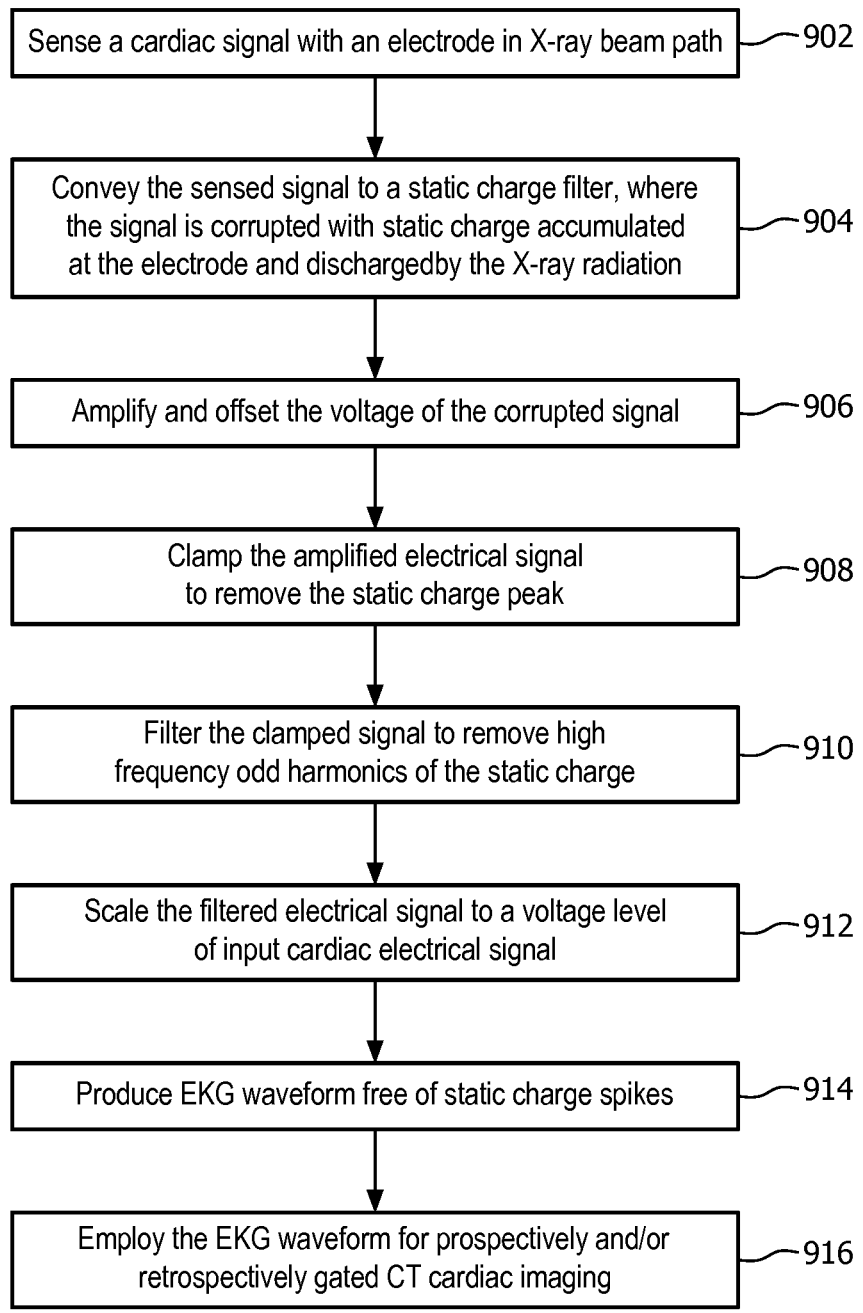
FIG. 9 illustrates an example method for removing static charge corrupting an EKG waveform, where the static charge is a results of X-ray induced discharge of static charge accumulated on an EKG electrode and/or lead in the X-ray beam path.

FIG. 9 illustrates an example method for removing static charge corrupting an EKG waveform, where the static charge is a results of X-ray induced discharge of static charged accumulated on an EKG electrode and/or lead in the X-ray beam path.

At 902, cardiac electrical signals are sensed by EKG electrodes, where at least one of the electrodes is in a path of an X-ray beam, and the at least one of the electrodes has accumulated static charged that is discharged by the X-ray radiation incident on the at least one of the electrodes through at least one of the leads. Additionally or alternatively, at least one of the leads in the path of the X-ray beam has accumulated static charge that is discharged by the X-ray radiation incident on the at least one of the leads.

Figure 3:
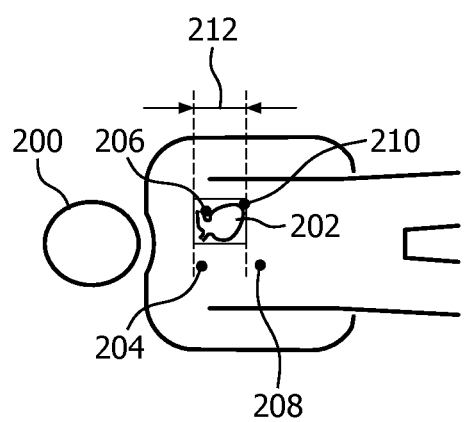
FIG. 3 schematically illustrates example placement of the EKG electrodes on a patient with at least one electrode in the X-ray beam path.

At 904, the cardiac electrical signals and the discharged static charge are electrically routed to a static charge filter, wherein the static charge filter processes one or more of the corrupted cardiac electrical signals from the different electrodes through separate channels. The corrupted cardiac electrical are conveyed through conventional EKG cables such as those shown in FIG. 3 and/or otherwise.

At 906, the corrupted cardiac electrical signal received by the static charge filter, which includes both the cardiac electrical signals and the discharged static charge, is amplified and offset. As discussed herein, the amplification is based on the voltage clamping level of the limiter and the offset keeps the RMS value close to zero (e.g., ±10 mV).

At 908, the amplified and offset signal is clamped based on the clamping threshold of a limiter, which removes static charge spike(s).

At 910, high frequency odd harmonics resulting from the clamping are filtered by a low pass filter.

At 912, the filtered signal is scaled by a second amplifier so that the output cardiac electrical signals have an amplitude corresponding to the amplitude of the input cardiac electrical signals.

At 914, the processed cardiac electrical signals are conveyed to an EKG monitor, which processes these signals and produces a waveform such as the EKG waveform 100 (FIG. 1), which will be free of the static charge spike 402 (FIG. 4).

At 916, one or more R peaks of the waveform are used to gate a cardiac scan to scan only during pre-determined windows within a cardiac phase of interest (prospective gating) or to locate project data corresponding to that window and phase after a scan in the projection data produced thereby (retrospective gating).

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A static charge filter for removing static charge in a cardiac electrical signal, comprising:
    a first amplifier configured to amplify an input signal by a first gain, producing an amplified signal, which includes the cardiac electrical signal and static charge from one or more electrodes in a path of an X-ray beam;
    a signal limiter configured to limit a maximum voltage of the amplified signal based on a predetermined clamping threshold, producing a voltage clamped signal;
    a filter configured to filter high frequency components of the voltage clamped signal, producing a filtered signal; and
    a second amplifier configured to scale an amplitude of the filtered signal using a second gain so that the cardiac electrical signal in an output signal has approximately a same voltage level as a voltage level of the cardiac electrical signal in the input signal.

2. The static charge filter of claim 1, further comprising:
    a separate processing channel for each of the one or more electrodes.

3. The static charge filter of claim 2, wherein only one of the separate processing channels is configured to remove static charge, and the other processing channels are pass-through.

4. The static charge filter of claim 2, wherein all of the separate processing channels are configured to remove static charge.

5. The static charge filter of claim 2, further comprising:
    a feedback loop of the first amplifier configured to automatically adjust the first gain so that the cardiac electrical signal in the amplified signal is at about the predetermined clamping threshold.

6. The static charge filter of claim 1, wherein the signal limiter comprises:
    an electrical path through the signal limiter;
    an electrical ground; and
    a pair of diodes electrically connected between the path and electrical ground in parallel and in reverse polarity, wherein a spike of the static charge in the amplified signal exceeding the predetermined clamping threshold turns one of the diodes on, clamping a maximum voltage of the amplified signal to the predetermined clamping threshold, and reducing the spike.

7. The static charge filter of claim 1, wherein the filter is a clock programmable low pass filter configured to reject the high frequency components out of band harmonics produced by clamping the amplified signal.

8. The static charge filter of claim 1, wherein the filter is a switched capacitor low pass filter.

9. The static charge filter of claim 1, wherein the first gain is a first value A and the second gain is at least a second value 1/A.

10. An imaging system, comprising:
    a gantry with an examination region;
    an X-ray radiation source configured to produce and transmit X-ray radiation that traverses the examination region;
    an X-ray sensitive detector array configured to detect the X-ray radiation traversing the examination region and generate projection data;
    one or more processors configured to reconstruct at least a sub-portion of the projection data and generate an image indicative thereof; and
    a static charge filter for removing static charge in a cardiac electrical signal, comprising:
        a first amplifier configured to amplify an input signal by a first gain, producing an amplified signal, which includes the cardiac electrical signal and static charge from one or more electrodes in a path of an X-ray beam;
        a signal limiter configured to limit a maximum voltage of the amplified signal based on a predetermined clamping threshold, producing a voltage clamped signal;
        a filter configured to filter high frequency components of the voltage clamped signal, producing a filtered signal; and
        a second amplifier configured to scale an amplitude of the filtered signal using a second gain so that a cardiac electrical signal in an output signal has approximately a same voltage level as a voltage level of the cardiac electrical signal in the input signal.

11. The imaging system of claim 10, further comprising:
an electrocardiogram monitor configured to process signals output by the static charge filter and produce an electrocardiogram waveform.

12. The imaging system of claim 11, wherein the one or more processors is configured to identify R peaks in the electrocardiogram waveform, and wherein the identified R peaks control an operation of the system during at least one of a prospectively gated cardiac scan or a retrospectively gated cardiac scan.

13. The imaging system of claim 10, further comprising:
a feedback loop of the first amplifier configured to automatically adjust the first gain so that the cardiac electrical signal in the amplified signal is at about the predetermined clamping threshold.

14. The imaging system of claim 10, wherein the signal limiter comprises:
an electrical path through the signal limiter;
an electrical ground; and
a pair of diodes electrically connected between the path and electrical ground in parallel and in reverse polarity, wherein a spike in the cardiac electrical signal exceeding the predetermined clamping threshold turns one of the diodes on, clamping a maximum voltage of the cardiac electrical signal to the predetermined clamping threshold, reducing the spike in the cardiac electrical signal.

15. A method for removing static charge in a cardiac electrical signal, comprising:
receiving a cardiac electrical signal from one or more electrodes in a path of an X-ray beam during an imaging examination, wherein the cardiac electrical signal includes static charge;
removing a static charge voltage spike from the received cardiac electrical signal, producing a static charge filtered cardiac electrical signal by:
amplifying the received cardiac electrical signal by a first gain, producing an amplified signal;
clamping a maximum voltage of the amplified signal based on a predetermined clamping threshold, producing a voltage clamped signal;
filtering high frequency out of band harmonics of the clamped signal, producing a filtered signal; and
scaling an amplitude of the filtered signal using a second gain, which produces an output signal having a voltage level at approximately a voltage level of the input cardiac electrical signal;
transmitting the static charge filtered cardiac electrical signal to an electrocardiogram monitor, which processes the static charge filtered cardiac electrical signal and produces an electrocardiogram waveform representing an electrical activity of a heart of the subject.

16. The method of claim 15, further comprising:
identifying an R peak in the electrocardiogram waveform;
triggering a scan during an acquisition window of a quiet phase of the heart based on the identified R peak; and
reconstructing projection data from the scan to generate an image of the heart for the acquisition window for the quiet phase.

17. The method of claim 15, further comprising:
identifying an R peak in the electrocardiogram waveform;
identifying a sub-set projection data corresponding to an acquisition window of a quiet phase of the heart from a set of projection data covering more than the acquisition window; and
reconstructing the sub-set of projection data to generate an image of the heart for the acquisition window for the quiet phase.

* * * * *